United States Patent
Qi et al.

(10) Patent No.: US 9,255,896 B2
(45) Date of Patent: Feb. 9, 2016

(54) GLASS PANEL STOCKING SYSTEM AND STOCKING METHOD

(71) Applicant: Shenzhen China Star Optoelectronics Technology Co., Ltd., Shenzhen, Guangdong (CN)

(72) Inventors: Minghu Qi, Shenzhen (CN); Chunhao Wu, Shenzhen (CN); Kunhsien Lin, Shenzhen (CN); Yongqiang Wang, Shenzhen (CN); Guokun Yang, Shenzhen (CN); Weibing Yang, Shenzhen (CN); Zenghong Chen, Shenzhen (CN); Yunshao Jiang, Shenzhen (CN); Zhiyou Shu, Shenzhen (CN); Chenyangzi Li, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 203 days.

(21) Appl. No.: 13/981,674

(22) PCT Filed: Jun. 21, 2013

(86) PCT No.: PCT/CN2013/077698
§ 371 (c)(1),
(2) Date: Jul. 25, 2013

(87) PCT Pub. No.: WO2014/201699
PCT Pub. Date: Dec. 24, 2014

(65) Prior Publication Data
US 2014/0368815 A1    Dec. 18, 2014

(30) Foreign Application Priority Data

Jun. 18, 2013    (CN) .......................... 2013 1 0243029

(51) Int. Cl.
*B32B 17/00* (2006.01)
*G01N 21/958* (2006.01)
(Continued)

(52) U.S. Cl.
CPC .............. *G01N 21/958* (2013.01); *B32B 17/00* (2013.01); *H01L 21/67259* (2013.01); *H01L 21/68* (2013.01)

(58) Field of Classification Search
CPC ................... H01L 21/67259; H01L 21/67265; H01L 21/67754; H01L 21/67757; G01N 21/13; G01N 21/958; B25J 11/0095
USPC ................................... 356/239.2; 414/222.07
See application file for complete search history.

(56) References Cited

U.S. PATENT DOCUMENTS

2006/0245860 A1 * 11/2006 Moriya et al. ................. 414/279
2006/0286700 A1    12/2006 Yoon
(Continued)

FOREIGN PATENT DOCUMENTS

CN    2390245 Y    8/2000
CN    1692487 A    11/2005
(Continued)

*Primary Examiner* — Ernesto Suarez
*Assistant Examiner* — Ronald Jarrett
(74) *Attorney, Agent, or Firm* — Andrew C. Cheng

(57) ABSTRACT

The present invention provides a glass panel stocking system and a stocking method. The stocking system includes a loading and unloading port and a crane. The loading and unloading port functions to receive a cassette that contains glass panels to position thereon. The crane functions to move a cassette that contains glass panels. The crane includes a chassis, a carrying fork mounted on the chassis and movable for extension and retraction with respect to the chassis, and a mapping bar mounted on the chassis and located above the carrying fork. The carrying fork functions to carry the cassette that contains the glass panels and move the cassette that contains the glass panels to the mapping bar so that the mapping bar is allowed to carry out inspection and counting of the glass panels received in the cassette that contains the glass panels.

4 Claims, 5 Drawing Sheets

(51) Int. Cl.
*H01L 21/68* (2006.01)
*H01L 21/67* (2006.01)

(56) References Cited

U.S. PATENT DOCUMENTS

2008/0232937 A1* 9/2008 Abe .................. H01L 21/67265
414/222.02

2010/0111650 A1* 5/2010 Quach et al. .................. 414/221

FOREIGN PATENT DOCUMENTS

| CN | 1885110 A | 12/2006 |
| CN | 1891591 A | 1/2007 |
| CN | 101026116 A | 8/2007 |
| CN | 102050330 A | 5/2011 |
| JP | 7-231031 A | 8/1995 |
| WO | WO9205920 A | 4/1992 |

* cited by examiner

GLASS PANEL STOCKING SYSTEM AND STOCKING METHOD

BACKGROUND OF THE INVENTION

1. Field of the Invention

The present invention relates to the field of the manufacture of glass panels, and in particular to a glass panel stocking system and a stocking method.

2. The Related Arts

Liquid crystal display (LCD) has a variety of advantages, such as thin device body, low power consumption, and being free of radiation, and is thus widely used. Most of the LCDs that are currently available in the market are backlighting LCDs, which comprise an enclosure, a liquid crystal panel arranged in the enclosure, and a backlight module that is arranged in the enclosure. The operation principle of the liquid crystal panel is that liquid crystal molecules are interposed between two parallel glass substrates and the liquid crystal molecules are controlled to rotate by the application of a driving voltage to the two glass substrates in order to refract out light emitting from the backlight module for generating images. Since the liquid crystal panel itself does not emit light, light must be provided by the backlight module in order to normally display images. Thus, the backlight module is one of the key components of an LCD. The backlight module can be classified in two types, namely side-edge backlight module and direct backlight module, according to the position where light gets incident. The direct backlight module comprises a light source, such as a cold cathode fluorescent lamp (CCFL) or a light-emitting diode (LED), which is arranged at the backside of the liquid crystal panel to form a planar light source that directly provides lighting to the liquid crystal panel. The side-edge backlight module comprises an LED light bar, serving as a backlight source, which is arranged at an edge of a backplane to be located rearward of one side of the liquid crystal panel. The LED light bar emits light that enters a light guide plate (LGP) through a light incident face of the light guide plate and is projected out of a light emergence face of the light guide plate, after being reflected and diffused, to pass through an optic film assembly to form a planar light source for the liquid crystal panel.

In a manufacturing process of the liquid crystal panel, before the glass panels are assembled, they are packaged first, generally packaged in a cassette (CST), and then stacked in a storage zone for subsequent use in a liquid crystal display assembling operation.

Referring to FIGS. 1 and 2, a conventional way of stacking glass panels is carried out with a stocker (STK) system. The stocker system comprises a crane 100, which functions to move a cassette 300 that receives glass panels 302 therein; and a loading and unloading port 500 on which a cassette 300 that contains glass panels 302 therein can be positioned, a mapping bar 520 being provided at the site where the loading and unloading port 500 for inspecting and counting the glass panels 302 received in the cassette 300. A conventional mapping bar 520 generally comprises electro-optical transducers 522 to scan the glass panels 302 contained in the cassette 300 in a top-down layer-by-layer manner in order to carry out inspection and count of the glass panels 302. The operation efficiency is low and further, a mapping bar 520 is required at each loading and unloading port 500, leading to a large number of mapping bars 520 used and thus an increased cost. This is adverse to cost control.

SUMMARY OF THE INVENTION

An object of the present invention is to provide a glass panel stocking system, which comprises a mapping bar for inspecting and counting glass panels contained in a cassette, which is mounted to a crane so as to carry out inspection and counting of the glass panels contained in the cassette at the same time when the crane moves the cassette, whereby the efficiency of stocking glass panels is increased and the number of mapping bars used is decreased so as to lower down the manufacture cost.

Another object of the present invention is to provide a glass panel stocking method, which performs inspection and counting of glass panels contained in a cassette at the same time when a crane is operated to move the cassette, whereby the efficiency of stocking glass panels is increased and the number of mapping bars used is decreased so as to lower down the manufacture cost.

To achieve the above objects, the present invention provides a glass panel stocking system, which comprises: a loading and unloading port and a crane. The loading and unloading port functions to receive a cassette that contains glass panels to position thereon. The crane functions to move a cassette that contains glass panels. The crane comprises a chassis, a carrying fork mounted on the chassis and movable for extension and retraction with respect to the chassis, and a mapping bar mounted on the chassis and located above the carrying fork. The carrying fork functions to carry the cassette that contains the glass panels and move the cassette that contains the glass panels to the mapping bar so that the mapping bar is allowed to carry out inspection and counting of the glass panels received in the cassette that contains the glass panels.

The carrying fork comprises a mounting section mounted to the chassis and a carrying section movably mounted to the mounting section.

The mapping bar comprises a support rack mounted to the chassis, a plurality of transducers attached to the support rack, and a counter unit mounted in the chassis and electrically connected to the plurality of transducers.

The number of the transducers corresponds to the number of glass panels receivable in the cassette that contains the glass panels.

The cassette that contains the glass panels has a sidewall facing the mapping bar and comprising openings corresponding to the transducers, whereby when the mapping bar carries out inspection and counting of the glass panels received in the cassette that contains the glass panels, the transducers are inserted through the openings into the cassette that contains the glass panels in such a way that the transducers are respectively located under the glass panels to be inspected and counted thereby, when one of the transducers detects the glass panel corresponding thereto exists, the counter unit counts the glass panel; and when one of the transducers does not detect the existence of the glass panel corresponding thereto, the layer is marked vacant and the counter unit does not count the glass panel.

The present invention also provides a glass panel stocking method, which comprises the following steps:

(1) providing a crane and a cassette that contains glass panels, wherein the crane comprises a chassis, a carrying fork mounted on the chassis and movable for extension and retraction with respect to the chassis, and a mapping bar mounted on the chassis and located above the carrying fork;

(2) extending out the carrying fork to allow the cassette that contains the glass panels to be positioned on the carrying fork;

(3) retracting back the carrying fork so as to move the cassette that contains the glass panels toward the mapping bar;

(4) the mapping bar carrying out inspection and counting of the glass panels received in the cassette that contains the glass panels; and (5) after completion of the inspection and counting by the mapping bar, the crane moving the cassette that contains the glass panels to the loading and unloading port.

The carrying fork comprises a mounting section mounted to the chassis and a carrying section movably mounted to the mounting section.

The mapping bar comprises a support rack mounted to the chassis, a plurality of transducers attached to the support rack, and a counter unit mounted in the chassis and electrically connected to the plurality of transducers.

The number of the transducers corresponds to the number of glass panels receivable in the cassette that contains the glass panels.

In step (4), the cassette that contains the glass panels has a sidewall facing the mapping bar and comprising openings corresponding to the transducers, whereby when the mapping bar carries out inspection and counting of the glass panels received in the cassette that contains the glass panels, the transducers are inserted through the openings into the cassette that contains the glass panels in such a way that the transducers are respectively located under the glass panels to be inspected and counted thereby, when one of the transducers detects the glass panel corresponding thereto exists, the counter unit counts the glass panel; and when one of the transducers does not detect the existence of the glass panel corresponding thereto, the layer is marked vacant and the counter unit does not count the glass panel.

The present invention further provides a glass panel stocking method, which comprises the following steps:

(1) providing a crane and a cassette that contains glass panels, wherein the crane comprises a chassis, a carrying fork mounted on the chassis and movable for extension and retraction with respect to the chassis, and a mapping bar mounted on the chassis and located above the carrying fork;

(2) extending out the carrying fork to allow the cassette that contains the glass panels to be positioned on the carrying fork;

(3) retracting back the carrying fork so as to move the cassette that contains the glass panels toward the mapping bar;

(4) the mapping bar carrying out inspection and counting of the glass panels received in the cassette that contains the glass panels; and (5) after completion of the inspection and counting by the mapping bar, the crane moving the cassette that contains the glass panels to the loading and unloading port; and wherein the carrying fork comprises a mounting section mounted to the chassis and a carrying section movably mounted to the mounting section;

wherein the mapping bar comprises a support rack mounted to the chassis, a plurality of transducers attached to the support rack, and a counter unit mounted in the chassis and electrically connected to the plurality of transducers;

wherein the number of the transducers corresponds to the number of glass panels receivable in the cassette that contains the glass panels; and wherein in step (4), the cassette that contains the glass panels has a sidewall facing the mapping bar and comprising openings corresponding to the transducers, whereby when the mapping bar carries out inspection and counting of the glass panels received in the cassette that contains the glass panels, the transducers are inserted through the openings into the cassette that contains the glass panels in such a way that the transducers are respectively located under the glass panels to be inspected and counted thereby, when one of the transducers detects the glass panel corresponding thereto exists, the counter unit counts the glass panel; and when one of the transducers does not detect the existence of the glass panel corresponding thereto, the layer is marked vacant and the counter unit does not count the glass panel.

The efficacy of the present invention is that the present invention provides a glass panel stocking system and a stocking method, which arrange a mapping bar for inspecting and counting glass panels receives in a cassette on a crane, whereby inspection and counting of the glass panels received in the cassette can be carried out at the same time when the crane moves the cassette. Further, a plurality of transducers is provided to simultaneously carry out inspection scanning of the glass panels received in the same cassette so that the efficiency of stocking glass panels can be effectively increased and the manufacture cost lowered down. Further, since the present invention arranges the transducers to insert into the cassette to inspect and scan the glass panels, compared to the conventional way of carrying out scanning outside the cassette, the accuracy is heightened. Further, the glass panel stocking system and stocking method according to the present invention can effectively reduce the number of mapping bars arranged at the loading and unloading ports or completely eliminate the arrangement of mapping bars at the loading and unloading ports so as to further reduce the manufacture cost.

For better understanding of the features and technical contents of the present invention, reference will be made to the following detailed description of the present invention and the attached drawings. However, the drawings are provided for the purposes of reference and illustration and are not intended to impose limitations to the present invention.

BRIEF DESCRIPTION OF THE DRAWINGS

The technical solution, as well as other beneficial advantages, of the present invention will be apparent from the following detailed description of embodiments of the present invention, with reference to the attached drawing. In the drawing.

DETAILED DESCRIPTION OF THE PREFERRED EMBODIMENTS

To further expound the technical solution adopted in the present invention and the advantages thereof, a detailed description is given to a preferred embodiment of the present invention and the attached drawings.

Figure 1:
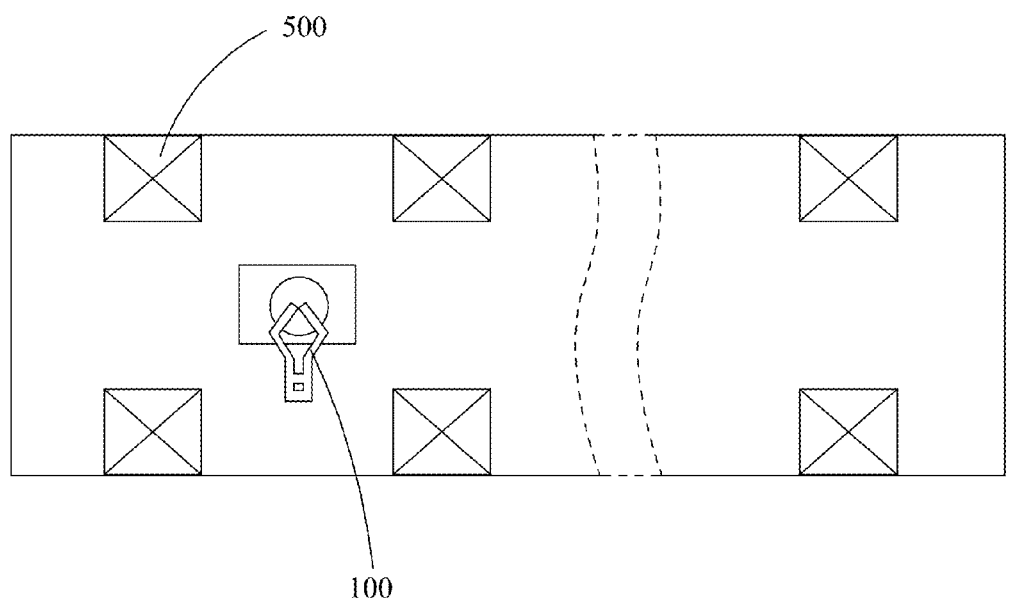
FIG. 1 is a schematic view showing the distribution of loading and unloading ports in a conventional stocker system.
Figure 2:
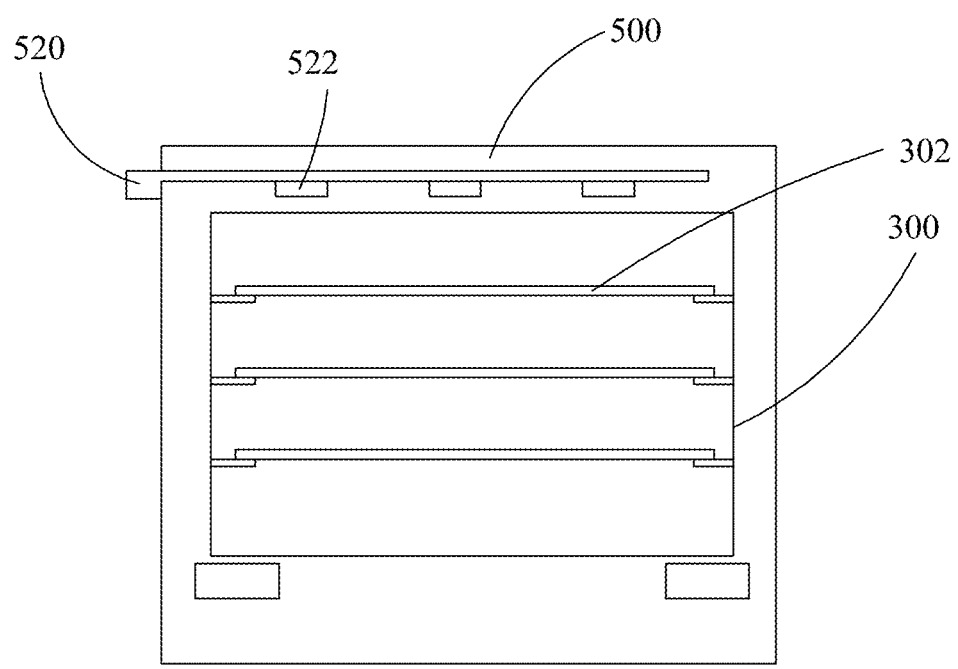
FIG. 2 is a schematic view showing an inspection and counting operation of glass panels located at a loading and unloading port carried out by the conventional stocker system.
Figure 3:
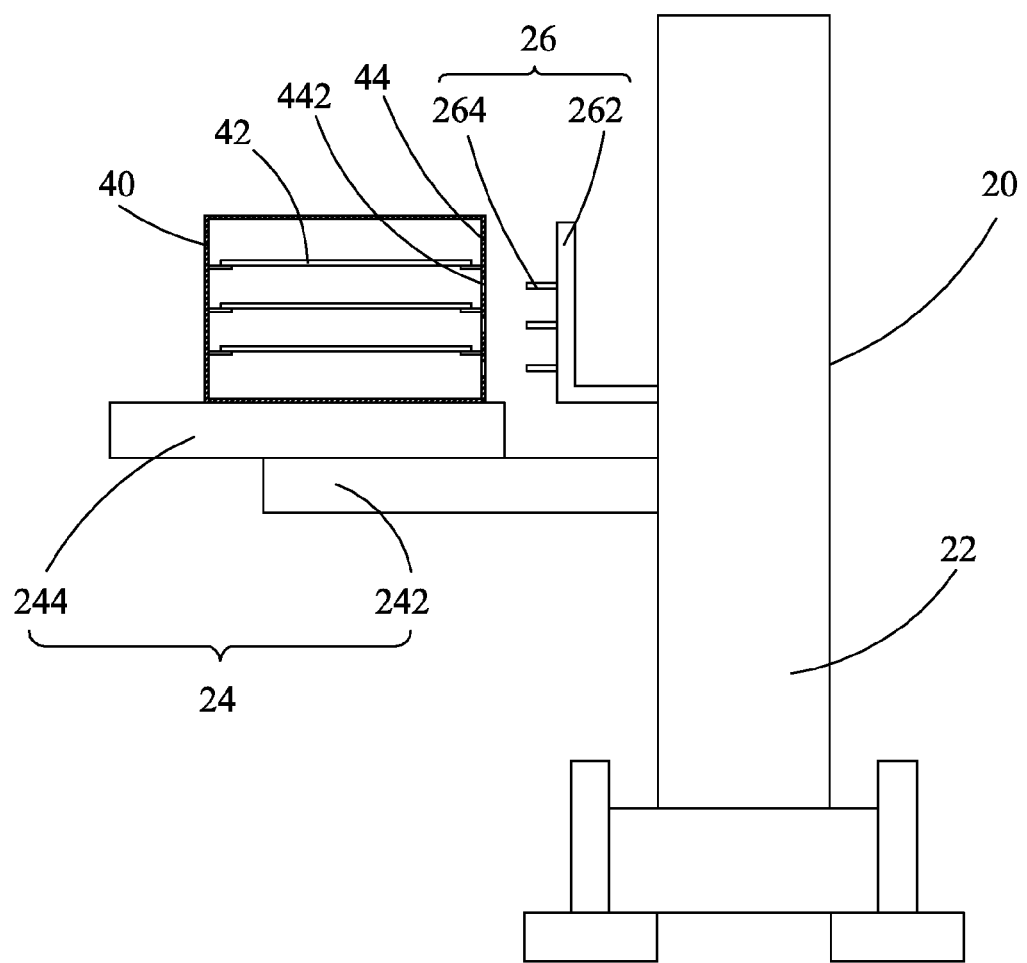
FIG. 3 is a schematic view showing a crane of a glass panel stocking system according to the present invention moving a cassette.
Figure 4:
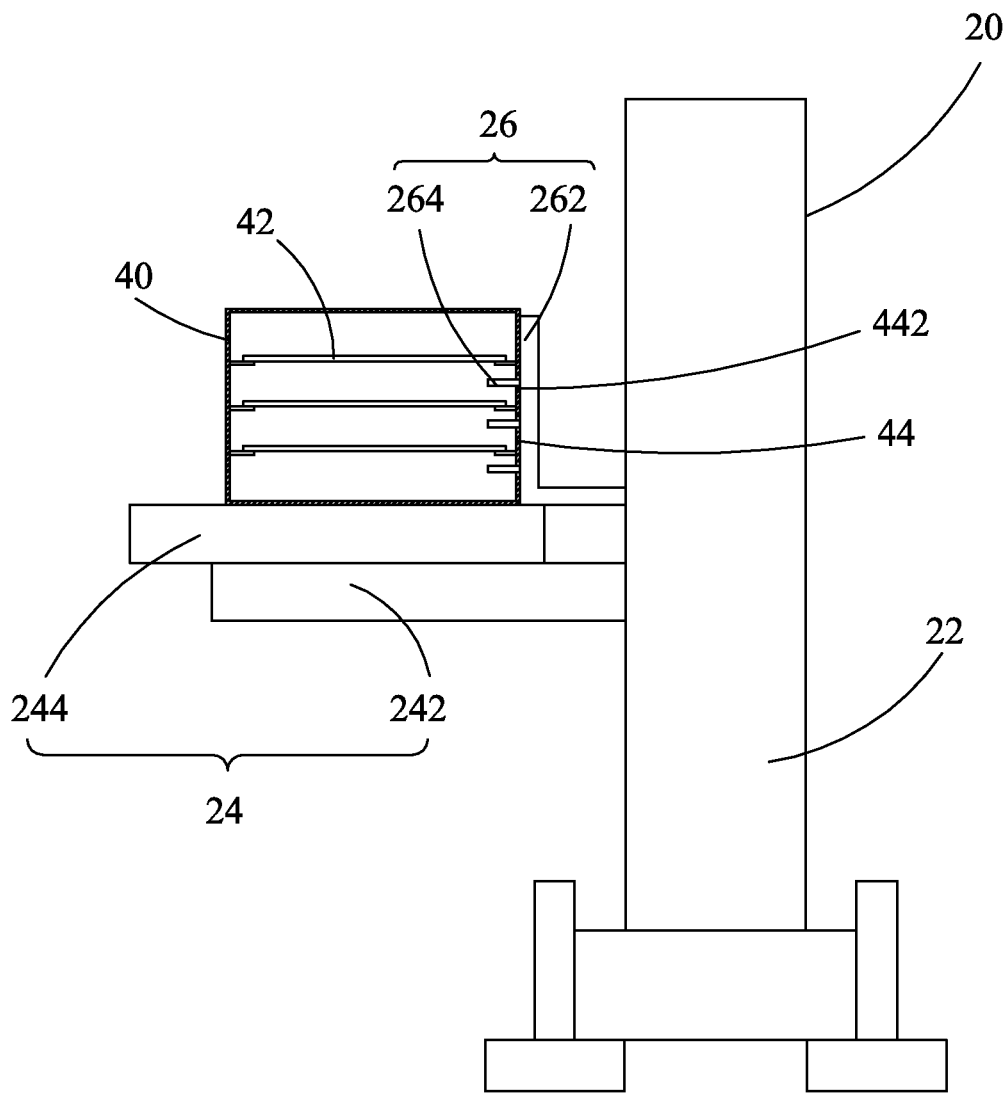
FIG. 4 is a schematic view showing an inspection and counting operation of glass panels contained in the cassette carried out by the crane of the glass panel stocking system according to the present invention.

Referring to FIGS. 3 and 4, the present invention provides a glass panel stocking system, which comprises: a loading and unloading port (not shown) and a crane 20. The loading and unloading port functions to receive a cassette 40 that contains glass panels 42 to position thereon. The crane 20 functions to move a cassette 40 that contains glass panels 42. The crane 20 comprises a chassis 22, a carrying fork 24 mounted on the chassis 22 and movable for extension and retraction with respect to the chassis 22, and a mapping bar 26 mounted on the chassis 22 and located above the carrying fork 24. The carrying fork 24 functions to carry a cassette 40 that contains glass panels 42 and move the cassette 40 that contains the glass panels 42 to the mapping bar 26 so that the mapping bar 26 may carry out inspection and counting of the glass panels 42 received in the cassette 40 that contains the glass panels 42. The present invention arranges the mapping bar 26 that carries out inspection and counting of the glass panels 42 received in the cassette 40 that contains the glass panels 42 on the crane 20, whereby an inspection and counting operation of the glass panels 42 received in the cassette 40 that contains the glass panels 42 can be carried out at the same time when the crane 20 moves the cassette 40 that contains the glass panels 42 so as to effectively increase the efficiency of stocking the glass panels 42 and lower down the manufacture cost.

Specifically, the carrying fork 24 comprises a mounting section 242 mounted to the chassis 22 and a carrying section 244 movably mounted to the mounting section 242. The mapping bar 26 comprises a support rack 262 mounted to the chassis 22, a plurality of transducers 264 attached to the support rack 262, and a counter unit (not shown) mounted in the chassis 22 and electrically connected to the plurality of transducers 264. The counter unit carries out inspection and counting according to the scanning inspection of the plurality of transducers 264. The location where the counter unit is mounted is not limited to be inside the chassis 22 and can be changed according to practical requirements. Preferably, the number of the transducers 264 corresponds to the number of glass panels 42 that can be received in the cassette 40 that contains the glass panels 42.

The cassette 40 that contains the glass panels 42 has a sidewall 44 facing the mapping bar 26 and comprising openings 442 corresponding to the transducers 264. Preferably, the cassette 40 that contains the glass panels 42 has four sidewalls all comprising openings 442 formed therein so that there is no need to concern about correspondence between the openings 422 and the transducers 264 when the cassette 40 that contains the glass panels 42 is positioned on the carrying section 244. The operation efficiency can thus be enhanced.

The carrying section 244 carries the cassette 40 that contains the glass panels 42 and moves toward the chassis 22 to bring the cassette 40 that contains the glass panels 42 to approach the mapping bar 26, in such a way that the transducers 264 of the mapping bar 26 are allowed to respectively insert through the openings 442 into the cassette 40 that contains the glass panels 42 with the transducers 264 respectively located under the glass panels 42 to be inspected and counted thereby. During the process of moving the cassette 40 that contains the glass panels 42 toward the loading and unloading port, the transducers 264 are operated to scan the glass panels 42, whereby when a transducer 264 detects a glass panel 42 corresponding thereto exists, the counter unit counts the glass panel 42; and when a transducer 264 does not detect the existence of a glass panel 42 corresponding thereto, the layer is marked vacant and the counter unit does not count it, and the inspection and counting of the glass panels 42 received in the cassette 40 that contains the glass panels 42 can then be completed. During such a process, the plurality of transducers 264 simultaneously carries out inspection and scanning of the glass panels 42 received in the same cassette 40 that contains the glass panels 42 so that the operation efficiency is high. Further, since the transducers 264 are inserted through the openings 442 into the cassette 40 that contains the glass panels 42 to inspect and scan the glass panels 42, compared to the conventional way of using three transducers located outside a cassette to carry out inspection and scanning of glass panels, the present invention provides increased accuracy of inspection.

Figure 5:
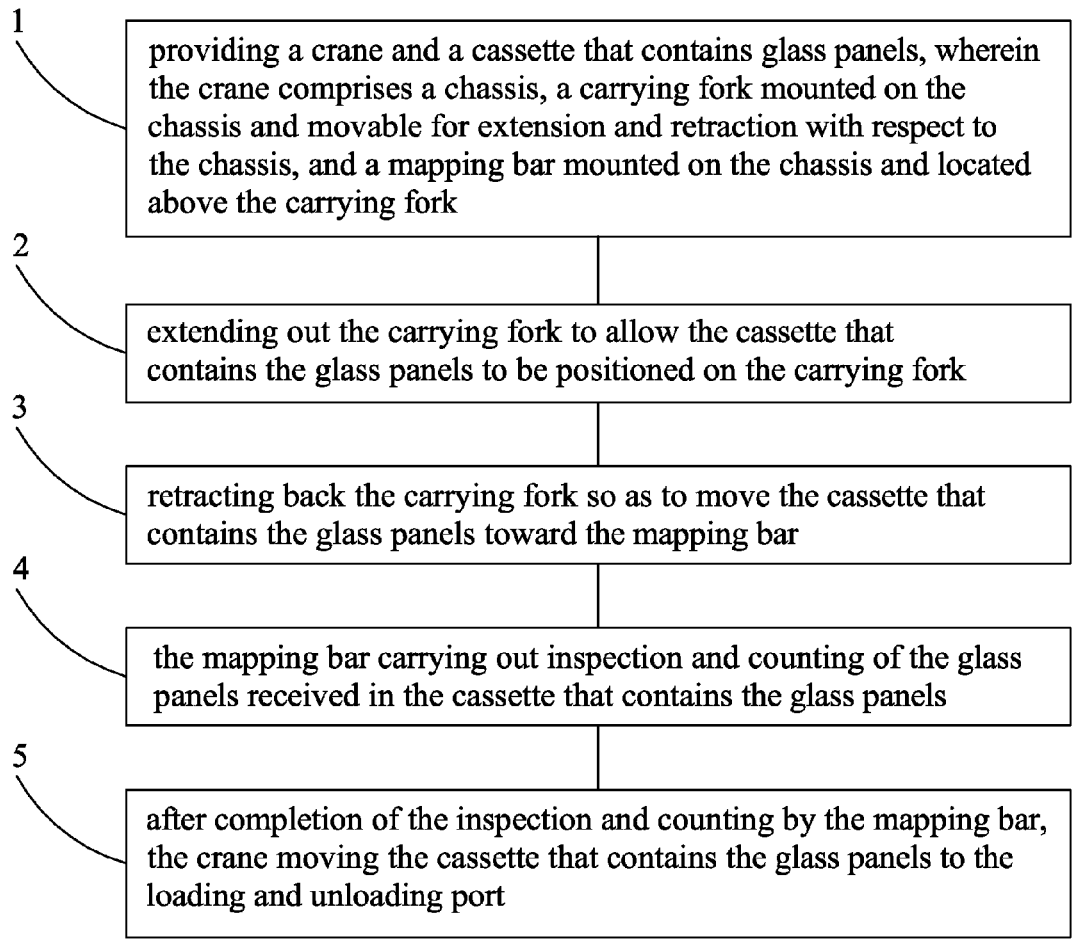
FIG. 5 is a flow chart illustrating a glass panel stocking method according to the present invention.

Referring to FIG. 5, as well as FIGS. 3 and 4, the present invention further provides a glass panel stocking method, which comprises the following steps:

Step 1: providing a crane 20 and a cassette 40 that contains glass panels 42, wherein the crane 20 comprises a chassis 22, a carrying fork 24 mounted on the chassis 22 and movable for extension and retraction with respect to the chassis 22, and a mapping bar 26 mounted on the chassis 22 and located above the carrying fork 24.

Specifically, the carrying fork 24 comprises a mounting section 242 mounted to the chassis 22 and a carrying section 244 movably mounted to the mounting section 242. The mapping bar 26 comprises a support rack 262 mounted to the chassis 22, a plurality of transducers 264 attached to the support rack 262, and a counter unit (not shown) mounted in the chassis 22 and electrically connected to the plurality of transducers 264. The counter unit carries out inspection and counting according to the scanning of the plurality of transducers 264. The location where the counter unit is mounted is not limited to be inside the chassis 22 and can be changed according to practical requirements. Preferably, the number of the transducers 264 corresponds to the number of glass panels 42 that can be received in the cassette 40 that contains the glass panels 42.

The cassette 40 that contains the glass panels 42 has a sidewall 44 facing the mapping bar 26 and comprising openings 442 corresponding to the transducers 264. Preferably, the cassette 40 that contains the glass panels 42 has four sidewalls all comprising openings 442 formed therein so that there is no need to concern about correspondence between the openings 422 and the transducers 264 when the cassette 40 that contains the glass panels 42 is positioned on the carrying section 244. The operation efficiency can thus be enhanced.

Step 2: extending out the carrying fork 24 to allow the cassette 40 that contains the glass panels 42 to be positioned on the carrying fork 24.

The cassette 40 that contains the glass panels 42 is positioned on the carrying section 244 of the carrying fork 24.

Step 3: retracting back the carrying fork 24 so as to move the cassette 40 that contains the glass panels 42 toward the mapping bar 26.

The carrying section 244 of the carrying fork 24 is moved with respect to the mounting section 242 toward the chassis 22 so as to bring the cassette 40 that contains the glass panels 42 to approach the mapping bar 26, whereby the transducers 264 of the mapping bar 26 are inserted through the openings 442 into the cassette 40 that contains the glass panels 42 with the transducers 264 respectively located under the glass panels 42 to be inspected and counted thereby.

Step 4: the mapping bar 26 carrying out inspection and counting of the glass panels 42 received in the cassette 40 that contains the glass panels 42.

The transducers 264 of the mapping bar 26 are operated to scan the glass panels 42, whereby when a transducer 264 detects a glass panel 42 corresponding thereto exists, the counter unit counts the glass panel 42; and when a transducer 264 does not detect the existence of a glass panel 42 corresponding thereto, the layer is marked vacant and the counter unit does not count it, and the inspection and counting of the glass panels 42 received in the cassette 40 that contains the glass panels 42 can then be completed.

Step 5: after completion of the inspection and counting by the mapping bar, the crane 20 moving the cassette 40 that contains the glass panels 42 to the loading and unloading port (not shown).

It is noted that during the process of moving the cassette 40 that contains the glass panels 42 to the loading and unloading port according to the present invention, the transducers 264 carry out scanning of the glass panels 42 to complete the inspection and counting of the glass panels 42 received in the cassette 40 that contains the glass panels 42. During such a process, the plurality of transducers 264 simultaneously carries out inspection and scanning of the glass panels 42 received in the same cassette 40 that contains the glass panels 42 so that the efficiency of stocking glass panels can be effectively increased and the manufacture cost lowered down. Further, since the transducers 264 are inserted through the openings 442 into the cassette 40 that contains the glass panels 42 to inspect and scan the glass panels 42, compared to the conventional way of using three transducers located outside a cassette to carry out inspection and scanning of glass panels, the present invention provides increased accuracy of inspection In summary, the glass panel stocking system and stocking method according to the present invention arrange a mapping bar for inspecting and counting glass panels receives in a cassette on a crane, whereby inspection and counting of the glass panels received in the cassette can be carried out at the same time when the crane moves the cassette. Further, a plurality of transducers is provided to simultaneously carry out inspection scanning of the glass panels received in the same cassette so that the efficiency of stocking glass panels can be effectively increased and the manufacture cost lowered down. Further, since the present invention arranges the transducers to insert into the cassette to inspect and scan the glass panels, compared to the conventional way of carrying out scanning outside the cassette, the accuracy is heightened. Further, the glass panel stocking system and stocking method according to the present invention can effectively reduce the number of mapping bars arranged at the loading and unloading ports or completely eliminate the arrangement of mapping bars at the loading and unloading ports so as to further reduce the manufacture cost.

Based on the description given above, those having ordinary skills of the art may easily contemplate various changes and modifications of the technical solution and technical ideas of the present invention and all these changes and modifications are considered within the protection scope of right for the present invention.

What is claimed is:

1. A glass panel stocking system, comprising: a loading and unloading port and a crane, the loading and unloading port functioning to receive a cassette that contains glass panels to position thereon, the crane functioning to move a cassette that contains glass panels, the crane comprising a chassis, a carrying fork mounted on the chassis and movable for extension and retraction with respect to the chassis, and a mapping bar mounted on the chassis and located above the carrying fork, the carrying fork functioning to carry the cassette that contains the glass panels and move the cassette that contains the glass panels to the mapping bar so that the mapping bar is allowed to carry out inspection and counting of the glass panels received in the cassette that contains the glass panels;

wherein the mapping bar comprises a support rack mounted to the chassis, a plurality of transducers attached to the support rack, and a counter unit mounted in the chassis and electrically connected to the plurality of transducers;

wherein the number of the transducers corresponds to the number of glass panels receivable in the cassette that contains the glass panels and the transducers are positionable at locations respectively corresponding to the glass panels to simultaneously and respectively inspect and count the glass panels; and wherein the cassette that contains the glass panels has sidewalls each comprising openings corresponding in number and position to the glass panels to allow the transducers to be simultaneously and respectively inserted through the openings into the cassette and each located at a predetermined position with respect to the glass panels.

2. The glass panel stocking system as claimed in claim 1, wherein the carrying fork comprises a mounting section mounted to the chassis and a carrying section movably mounted to the mounting section.

3. A glass panel stocking method, comprising the following steps:
   (1) providing a crane and a cassette that contains glass panels, wherein the crane comprises a chassis, a carrying fork mounted on the chassis and movable for extension and retraction with respect to the chassis, and a mapping bar mounted on the chassis and located above the carrying fork;
   (2) extending out the carrying fork to allow the cassette that contains the glass panels to be positioned on the carrying fork;
   (3) retracting back the carrying fork so as to move the cassette that contains the glass panels toward the mapping bar;
   (4) the mapping bar carrying out inspection and counting of the glass panels received in the cassette that contains the glass panels; and
   (5) after completion of the inspection and counting by the mapping bar, the crane moving the cassette that contains the glass panels to the loading and unloading port;

wherein the mapping bar comprises a support rack mounted to the chassis, a plurality of transducers attached to the support rack, and a counter unit mounted in the chassis and electrically connected to the plurality of transducers; and wherein the number of the transducers corresponds to the number of glass panels receivable in the cassette that contains the glass panels and the transducers are positionable at locations respectively corresponding to the glass panels to simultaneously and respectively inspect and count the glass panels; and wherein the cassette that contains the glass panels has sidewalls each comprising openings corresponding in number and position to the glass panels to allow the transducers to be simultaneously and respectively inserted through the openings into the cassette and each located at a predetermined position with respect to the glass panels.

4. The glass panel stocking method as claimed in claim 3, wherein the carrying fork comprises a mounting section mounted to the chassis and a carrying section movably mounted to the mounting section.

* * * * *